(12) United States Patent
Hutchinson

(10) Patent No.: US 10,549,995 B2
(45) Date of Patent: Feb. 4, 2020

(54) OXYGEN GENERATORS

(71) Applicant: Molecular Oxygen Limited, Harlow (GB)

(72) Inventor: Peter Hutchinson, Harlow (GB)

(73) Assignee: Molecular Oxygen Limited, Harlow (GB)

(*) Notice: Subject to any disclaimer, the term of this patent is extended or adjusted under 35 U.S.C. 154(b) by 44 days.

(21) Appl. No.: 15/739,077

(22) PCT Filed: Jun. 24, 2016

(86) PCT No.: PCT/GB2016/051896
§ 371 (c)(1),
(2) Date: Dec. 21, 2017

(87) PCT Pub. No.: WO2016/207649
PCT Pub. Date: Dec. 29, 2016

(65) Prior Publication Data
US 2018/0186636 A1    Jul. 5, 2018

(30) Foreign Application Priority Data
Jun. 25, 2015 (GB) .................. 1511177.6

(51) Int. Cl.
*A61M 16/10* (2006.01)
*B01D 46/24* (2006.01)
*C01B 13/02* (2006.01)

(52) U.S. Cl.
CPC ..... *C01B 13/0296* (2013.01); *A61M 16/1005* (2014.02); *B01D 46/2403* (2013.01); *C01B 13/0218* (2013.01); *A61M 2202/0208* (2013.01)

(58) Field of Classification Search
CPC .. A61M 16/00; A61M 16/10; A61M 16/1005; A61M 2202/00; A61M 2202/02; A61M 2202/0208; B01D 46/00; B01D 46/24; B01D 46/2403; C01B 13/00–0203; C01B 13/0218; C01B 13/0296
See application file for complete search history.

(56) References Cited

U.S. PATENT DOCUMENTS

| | | | |
|---|---|---|---|
| 3,615,250 A | 10/1971 | Vernon | |
| 3,736,104 A | 5/1973 | Churchill et al. | |
| 3,868,225 A | 2/1975 | Tidd | |
| 4,832,926 A * | 5/1989 | Schillaci | A62D 9/00 252/181.7 |

(Continued)

FOREIGN PATENT DOCUMENTS

| | | | |
|---|---|---|---|
| EP | 0736486 | 9/1996 | |
| WO | WO-2015087077 A1 * | 6/2015 | ......... C01B 13/0218 |

OTHER PUBLICATIONS

International Search Report of PCT/GB2016/051896 dated Oct. 4, 2016, 3 pp.

*Primary Examiner* — Natasha E Young
(74) *Attorney, Agent, or Firm* — Lathrop Gage LLP

(57) ABSTRACT

A chemical core for an oxygen generator. The chemical core is capable on ignition of producing oxygen by chemical reaction. A first end of the chemical core has a smaller cross-sectional area than a second end of the chemical core such that the ratio of the cross-sectional area of the second end to the cross-sectional area of the second end is 0.20:1 or more.

7 Claims, 7 Drawing Sheets

(56) References Cited

U.S. PATENT DOCUMENTS

| | | | |
|---|---|---|---|
| 7,494,624 B2 * | 2/2009 | Crudace | A62B 21/00 422/120 |
| 2013/0259756 A1 | 10/2013 | Maroske et al. | |
| 2013/0280514 A1 * | 10/2013 | Lawrenson | A62B 21/00 428/292.1 |

* cited by examiner

OXYGEN GENERATORS

CROSS-REFERENCE TO RELATED APPLICATIONS

This application is a national stage application claiming priority to PCT/GB2016/051896, now WO/2016/207649, and filed on Jun. 24, 2016, which claims priority to Great Britain Patent Application Serial No. GB 1511177.6, filed on Jun. 25, 2015.

FIELD OF THE INVENTION

The present invention concerns oxygen generators. More particularly, but not exclusively, the present invention concerns portable oxygen candles that are used to provide breathable oxygen for medical use.

BACKGROUND OF THE INVENTION

Oxygen candles are well-known. Oxygen candles are devices that produce on demand a supply of oxygen by means of a chemical reaction. (The term "chemical reaction" is used herein to exclude electrolytic decomposition and other methods requiring an external source of energy.) An example of an oxygen candle is disclosed in WO 2009/030921 A2 (Molecular Products Group PLC) published 12 Mar. 2009.

A typical oxygen candle comprises a chemical core of an oxygen-containing substance, for example an alkali metal chlorate or perchlorate, in admixture with a catalyst that facilitates lower temperature decomposition of the chemical to oxygen and residual solids. The catalyst may be manganese dioxide or cobalt dioxide, for example, both of which reduce the temperature at which alkali metal chlorates decompose. The chemical core often also comprises a fuel such as iron.

A known oxygen candle is shown in FIG. 1. The oxygen candle 1 comprises a cylindrical chemical core 2 within an insulated housing 3. A first end of the oxygen candle 1 comprises an ignition apparatus 4, which is used to trigger the production of oxygen by the device. The ignition apparatus 4 may for example be a rotatable body, with a surface facing the chemical core 2 coated with a friction-ignitable substance such as phosphorus. A second end of oxygen candle 1 opposite the first end comprises an oxygen outlet 5. Within the insulated housing 3, between the oxygen outlet 5 and the chemical core 2, there is a filter 6, which contains filtration materials such as soda lime. The filter 6 is a disc-like cylinder a surface of which covers the entire inside surface of the insulated housing 3 of the second end of the oxygen candle 1. The oxygen candle 1 may also comprise a chamber (not shown in FIG. 1) to receive oxygen produced by the chemical core, to cool the oxygen before it is outputted through the oxygen outlet 5.

When a supply of oxygen is required, the ignition apparatus 4 is rotated so that the friction-ignitable substance on its coated surface is forced into contact with the surface of the chemical core 2. This causes an exothermic reaction to be generated, which initiates the chemical reaction that releases the oxygen the chemical core contains. The oxygen is initially released from the end of the chemical core 2 at the first end of the oxygen candle 1, and passes along the sides of the chemical core 2 within the insulated housing 3 along the arrows marked A, towards the oxygen outlet 5 at the opposite end of the oxygen candle 6. Before the oxygen passes out of the oxygen outlet 5 it passes through the filter 6, which removes unwanted reaction products from the oxygen supply, such as carbon dioxide, carbon monoxide and chlorine.

It is a disadvantage of the known oxygen candle 1 that not all unwanted reaction products are removed from the oxygen supply by the filter 6. The present invention seeks to solve or mitigate this problem. Alternatively and/or additionally, the invention seeks to provide an improved chemical core and an improved oxygen generator.

SUMMARY OF THE INVENTION

In accordance with a first aspect of the invention there is provided a chemical core for an oxygen generator, the chemical core being capable on ignition of producing oxygen by chemical reaction, wherein a first end of the chemical core has a larger cross-sectional area than a second end of the chemical core, such that the ratio of the cross-sectional area of the first end to the cross-sectional area of the second end is 1.20:1 or more.

When the chemical core is used in an oxygen generator in which the first end of the chemical core is ignited and oxygen is supplied from an oxygen outlet at the second end of the chemical core, the oxygen produced heats the chemical core as it passes from the first end to the second end. The increase in temperature causes the chemical reaction that releases the oxygen to occur more quickly. By having a smaller cross-sectional area at the second end, there is less of the chemical core undergoing the chemical reaction, so mitigating the effects of the heating in terms of the amount of oxygen produced and providing a steadier supply of oxygen.

For the avoidance of doubt, by a ratio of 1.20:1 or more, it is meant that the cross-sectional area of the first end of the chemical core divided by the cross-sectional area of the second end of the chemical core is 1.20 or a larger number. More preferably, the ratio of the cross-sectional area of the first end to the cross-sectional area of the second end is 1.33:1 or more. The ratio of the cross-sectional area of the first end to the cross-sectional area of the second end may be 1.3:1 or 1.4:1. The ratio of the cross-sectional area of the first end to the cross-sectional area of the second end may be 1.39:1. The ratio of the cross-sectional area of the first end to the cross-sectional area of the second end may be between 1.33:1 and 1:44 to 1, or between 1:3 and 1:5 to 1.

It will be appreciated that the edges of the faces of the first and second ends of the chemical core may be rounded or otherwise tapered, and so the relevant cross-sectional areas may be not be at the faces of the first and second ends.

Preferably, the chemical core comprises a first cylindrical portion and a second tapered portion. Further preferably, the chemical further comprises a second cylindrical portion of smaller cross-sectional area than the first cylindrical portion, wherein the tapered portion is positioned between the first cylindrical portion and the second cylindrical portion. This can provide a larger air gap between the chemical core and insulated housing of the oxygen generator, reducing the heating effect of the oxygen on the chemical core as it passes through the air gap.

It will be appreciated that the first and second cylindrical portions may themselves be slightly tapered, as this aids in the manufacture of the chemical core. (Chemical cores are conventionally manufactured by being pressed within a mould, and a slight taper aids in the release of the chemical core from the mould.)

As above, the ratio of the cross-sectional area of the first end to the cross-sectional area of the second end is 1.20:1 or more. More preferably, the ratio of the cross-sectional area of the first end to the cross-sectional area of the second end is 1.33:1 or more. The ratio of the cross-sectional area of the first end to the cross-sectional area of the second end may be 1.3:1 or 1.4:1. The ratio of the cross-sectional area of the first end to the cross-sectional area of the second end may be 1.39:1. The ratio of the cross-sectional area of the first end to the cross-sectional area of the second end may be between 1.33:1 and 1:44 to 1, or between 1:3 and 1:5 to 1.

The chemical may comprise metal chlorate or perchlorate. The chemical core may comprise a catalyst and a fuel. The catalyst may be manganese dioxide or cobalt dioxide. The fuel may be iron. Alternatively, the fuel may be magnesium.

In accordance with a second aspect of the invention there is provided an oxygen generator comprising:

an insulated housing comprising a first end and a second end opposite the first end;

a chemical core as described above positioned within the insulated housing so that the second end of the chemical core is at the second end of the insulated housing;

an ignition apparatus positioned at the first end of the insulated housing, for igniting a first end of the chemical core;

an oxygen outlet positioned at the second end of the insulated housing, for outputting oxygen produced by the chemical core;

a filter positioned within the second end of the insulated housing between the chemical core and the oxygen outlet, the filter being capable of removing at least one reaction product produced by the chemical reaction of the chemical core.

The filter may be capable of removing carbon dioxide, carbon monoxide and/or chlorine from the oxygen supply produced by the chemical core, for example. The filter may comprise soda lime.

The filter may be cylindrical, i.e. disk-shaped. More preferably, the filter extends towards the first end of the insulated housing between the outer surface of the chemical core and the inner surface of the insulated housing. In other words, the filter extends up the gap between the outer surface of the chemical core and the inner surface of the insulated housing. As such, the filter may be cup-shaped. Preferably, the filter is in contact with the surfaces of both the chemical core and the insulated housing. In the case that the chemical core has a tapered section, preferably the filter is in contact with the surface of all of the tapered section. In the case that the chemical core has a second cylindrical section, preferably the filter is in contact with the surface of all of the second cylindrical section. By having the filter in contact with the surfaces of both the chemical core and the insulated housing, the amount of filter through which the oxygen passes is maximised. This results in improved removal of unwanted reaction products from the oxygen supply produced by the chemical core. It also reduces the heating effect of the oxygen on the chemical core.

Preferably, the oxygen generator further comprises a cooling chamber positioned within the insulated housing having an inlet through which oxygen produced by the chemical core enters into the cooling chamber and an outlet through which cooled oxygen exits to the oxygen outlet.

In accordance with a third aspect of the invention there is provided an oxygen generator comprising:

an insulated housing comprising a first end and a second end opposite the first end;

a chemical core positioned within the insulated housing, the chemical core being capable on ignition of producing oxygen by chemical reaction;

an ignition apparatus positioned at the first end of the insulated housing, for igniting a first end of the chemical core;

an oxygen outlet positioned at the second end of the insulated housing, for outputting oxygen produced by the chemical core;

a filter positioned within the second end of the insulated housing between the chemical core and the oxygen outlet, the filter being capable of removing at least one reaction product produced by the chemical reaction of the chemical core, wherein the filter extends towards the first end of the insulated housing between the outer surface of the chemical core and the inner surface of the insulated housing.

Preferably, the filter is in contact with the surfaces of both the chemical core and the insulated housing. By having the filter in contact with the surfaces of both the chemical core and the insulated housing, the amount of filter through which the oxygen passes is maximised. This results in improved removal of unwanted reaction products from the oxygen supply produced by the chemical core. It also reduces the heating effect of the oxygen on the chemical core.

Preferably, the oxygen generator comprises a cooling chamber positioned within the insulated housing having an inlet through which oxygen produced by the chemical core enters into the cooling chamber and an outlet through which cooled oxygen exits to the oxygen outlet.

It will of course be appreciated that features described in relation to one aspect of the present invention may be incorporated into other aspects of the present invention.

DESCRIPTION OF THE DRAWINGS

Embodiments of the present invention will now be described by way of example only with reference to the accompanying schematic drawings of which.

DETAILED DESCRIPTION

An oxygen candle in accordance with a first embodiment of the invention is now described with reference to FIGS. 2 and 3.

Figure 1:
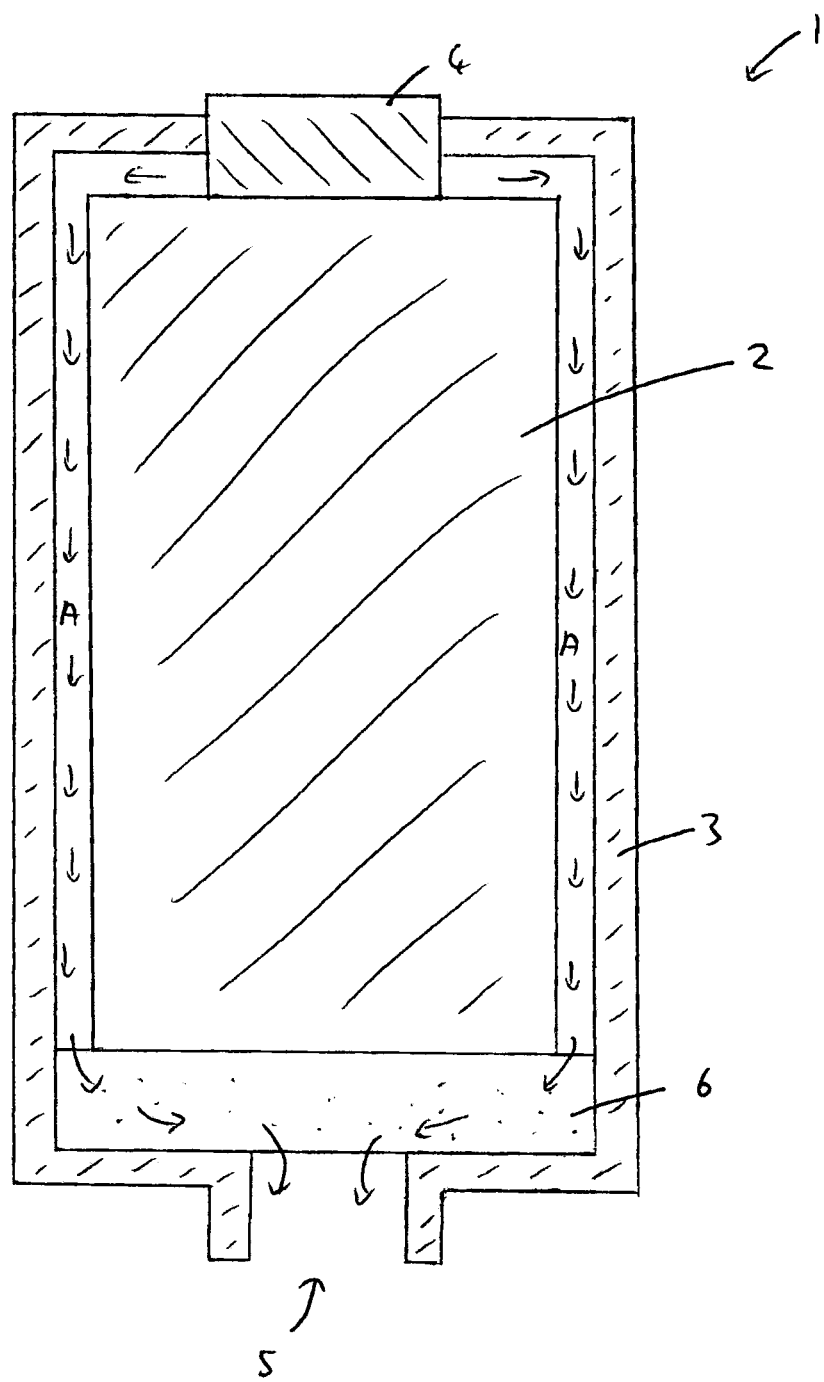
FIG. 1 is a cross-sectional view of a known oxygen candle.

Similarly to the known oxygen candle 1 shown in FIG. 1, the oxygen candle 100 of the first embodiment comprises an insulated housing 1 comprising an ignition apparatus 4 at a first end and an oxygen outlet 5 at a second end opposite the first end.

Figure 2:
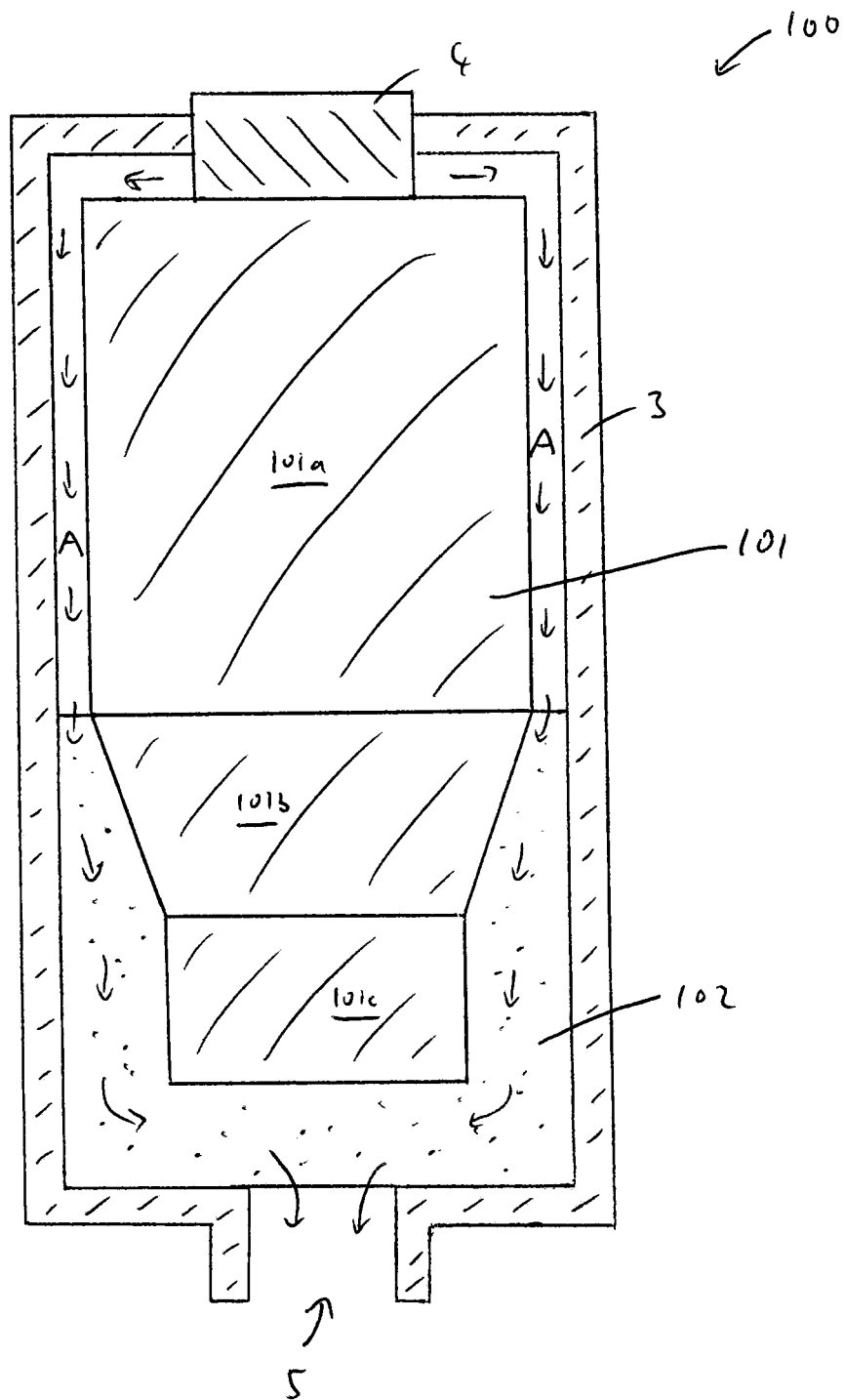
FIG. 2 is a cross-sectional view of an oxygen candle according to a first embodiment of the invention.

Again similarly to the known oxygen candle 1, the oxygen candle 100 comprises a chemical core 102, which is also shown in FIG. 2. However, while the chemical core 2 of the known oxygen candle 1 is cylindrical in shape, the chemical core 102 of the oxygen candle 1 has a first cylindrical section 101a, a tapered portion 101b, and second cylindrical portion 101c of narrower diameter than the first cylindrical section 101a. (Each of the first cylindrical section 101a, tapered portion 101b, and second cylindrical portion 101c is circular in cross-section.) The first cylindrical section 101a of the chemical core 101 is positioned at the first end of the oxygen candle 100 adjacent to the ignition apparatus 4, and the second cylindrical section 101c of the chemical core 101 is positioned at the second end of the oxygen candle 100 adjacent to the oxygen outlet 5.

Figure 3A:
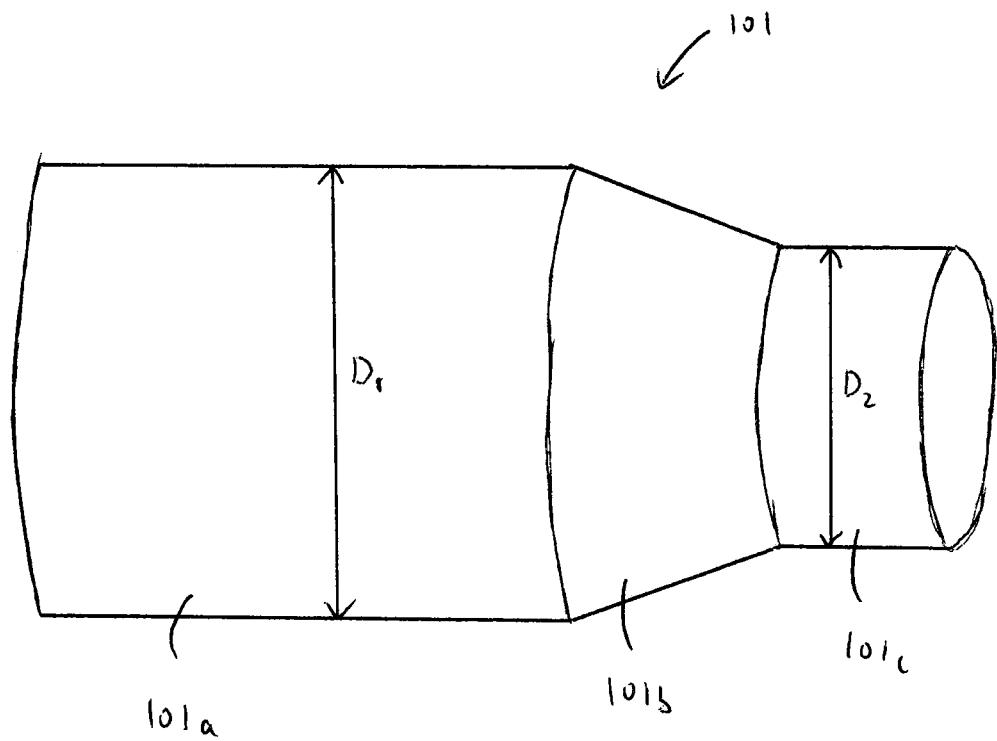
FIG. 3a is a perspective view of the chemical core of the oxygen candle of the first embodiment.

As shown in FIG. 3a, the first cylindrical section 101a has a diameter of $D_1$ and the second cylindrical section 101b has a diameter of $D_2$. The sections have cross-sectional areas of $\pi D_1^2/4$ and $\pi D_2^2/4$ respectively, and the ratio of $\pi D_1^2/4$ to $\pi D_2^2/4$ is 1.4 to 1, i.e. $D_1^2:D_2^2$ is 1.4:1.

Figure 3B:
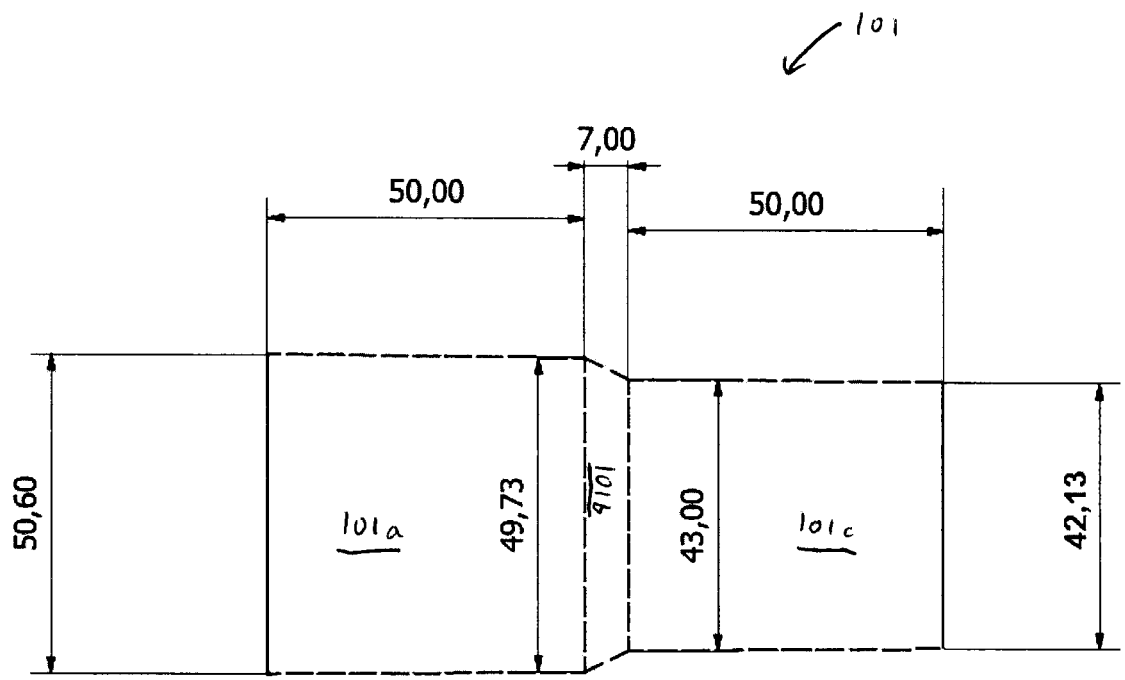
FIG. 3b is a cross-sectional view of the candle core with measurements shown.

FIG. 3b is a cross-sectional view of the chemical core 101, with measurements included. It will be appreciated that in practice, the first cylindrical section 101a and the second cylindrical section 101b will also be slightly tapered, as chemical cores are conventionally manufactured by being pressed within a mould and so a slight taper aids in the release of the chemical core from the mould.

As can be seen from FIG. 3b, the first cylindrical section 101a is of length 50 mm, the tapered section 101b is of length 7 mm, and the second cylindrical section 101c is of length 50 mm. The diameter of the first cylindrical section 101a is 50.6 mm at its widest end, tapering slowly to 49.73 mm at its end adjacent to the tapered section 101b. The tapered section 101b then tapers very quickly to 43 mm at its end adjacent to the second cylindrical section 101c. The second cylindrical section 101c then tapers slowly again to 42.13 mm at its narrowest end. From these measurements it can be calculated that the ratio of the cross-sectional area of the first cylindrical section 101a to the second cylindrical section 101a is at least 1:33 (comparing the narrowest part of the first cylindrical section 101a to the widest part of second cylindrical section 101a), at most 1:44 (comparing the widest part of the first cylindrical section 101a to the narrowest part of second cylindrical section 101a), and is 1:39 taking the midpoint of the sections 101a and 101c. (This compares to a maximum ratio of 1:1.1 for a conventional chemical core that tapers slowly all along its entire length, without any rapidly tapering section.)

Again similarly to the known oxygen candle 1, the oxygen candle 100 comprises a filter 102 at the second end of the oxygen candle 1, between the oxygen outlet 5 and the chemical core 101. However, the filter 102 is cup-shaped, so as well as having a disk-like portion that covers the entire inner surface of the insulated housing 3 of the oxygen candle 100, the filter 102 extends up the gap between the insulated housing 3 and the chemical core 101, so that its inside surface covers the outer surfaces of the second cylindrical portion 101c and tapered portion 101b of the chemical core 101, and its outer surface covers the facing inner surfaces of the insulated housing 3.

As with the known oxygen candle 1, when a supply of oxygen is required from the oxygen candle 100, the ignition apparatus 4 is rotated to initiate the chemical reaction that releases the oxygen from the chemical core. The oxygen is initially released from the end of the chemical core 101 at the first end of the oxygen candle 1, and again passes along the sides of the chemical core 101 within the insulated housing 3 along the arrows marked A, towards the oxygen outlet 5 at the opposite end of the oxygen candle 6. However, in the present embodiment the oxygen passes through the filter 102 in the regions of the tapered portion 101b and second cylindrical portion 101c of the chemical core 101, as well in the region between the end of the chemical core 101 and the oxygen outlet 5. It has been found that this results in much more effective removal of unwanted reaction products from the oxygen supply by the filter 102.

Figure 4:
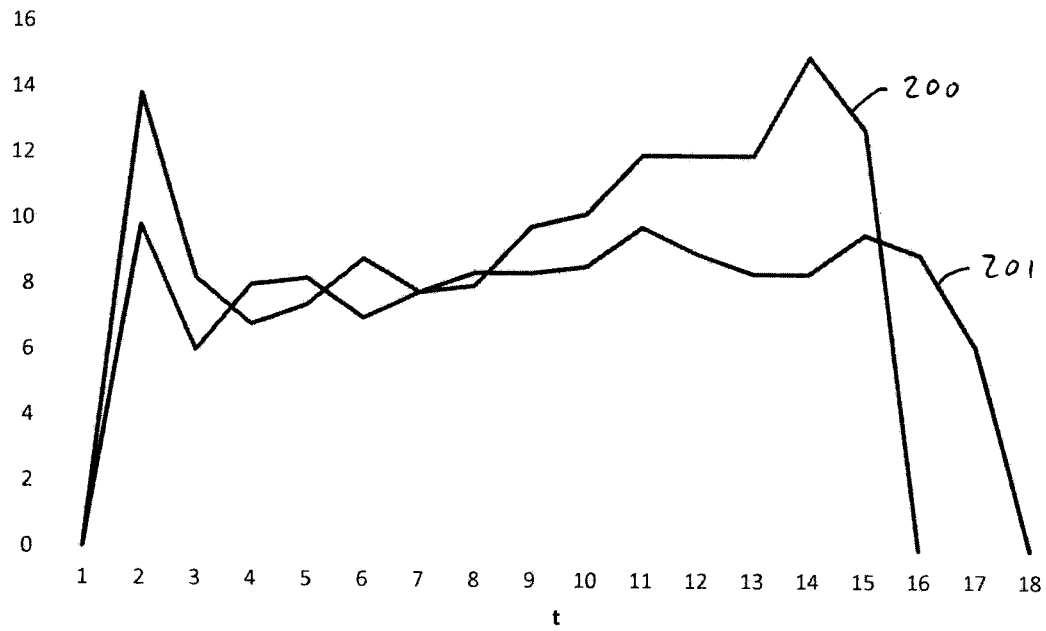
FIG. 4 is a graph showing the oxygen output over time of the known oxygen candle and the oxygen candle of the first embodiment.

In addition, this configuration has been found to provide an improved oxygen supply. FIG. 4 is a graph showing amount of oxygen L (in litres) output over time t (in minutes) by the known oxygen candle 1 and the oxygen candle 100 of first embodiment.

The output of the known oxygen candle 1 is shown by the line 200. As can be seen, initially at around 2 minutes the amount of oxygen output peaks at around 14 litres, and then drops down to around 7 litres before slowly increasing to a second peak of around 15 litres at around 14 minutes, and then drops sharply to zero at 16 minutes.

The output of the oxygen candle 100 of the first embodiment is shown by the line 201. In this case, initially the oxygen peaks at around 10 litres, and then continues to output oxygen at around that level until around 16 minutes, when it drops down to zero at 18 minutes. Thus, the oxygen candle 100 of the first embodiment provides both a steadier and a longer supply of oxygen.

Figure 5:
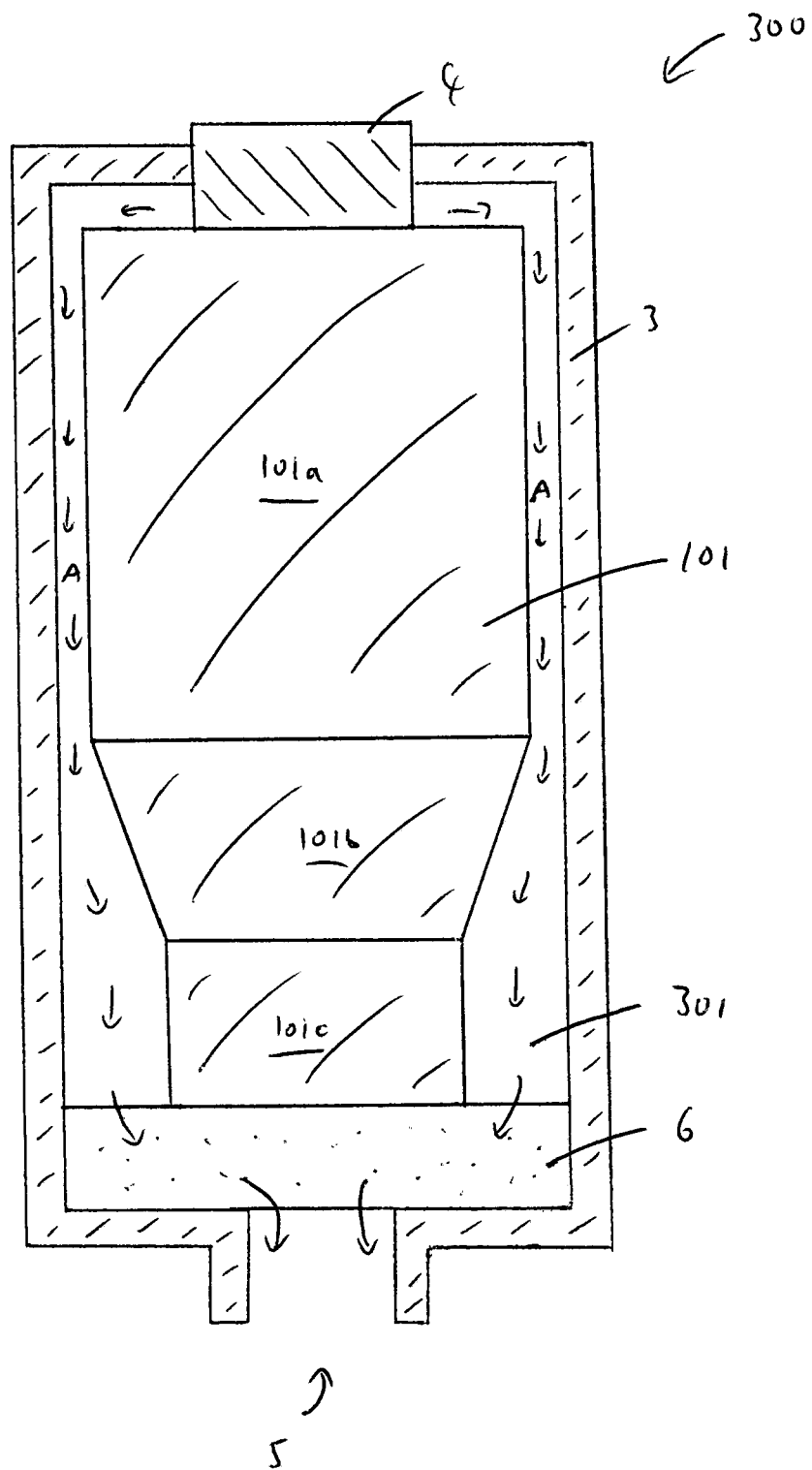
FIG. 5 is a cross-sectional view of an oxygen candle according to a second embodiment of the invention.

An oxygen candle in accordance with a second embodiment of the invention is now described with reference to FIG. 5. The oxygen candle 300 of the second embodiment is similar to the oxygen candle 100 of the first embodiment, expect that instead of the filter 102, the oxygen candle 300 comprises the filter 6 of the known oxygen candle 1.

While this is a less advantageous configuration than that of the oxygen candle 100, the reduced diameter of the end of the chemical core 101, and the corresponding larger gap 301 between the chemical core 101 and the inside of the insulated housing 3, can still result in a steadier and a longer supply of oxygen compared to the known oxygen candle 1. In addition, there is a greater area of surface of the filter 6 around the end of the chemical core 101 through which oxygen will enter, which can result in a more effective removal of unwanted reaction products compared to the known oxygen candle 1.

Figure 6:
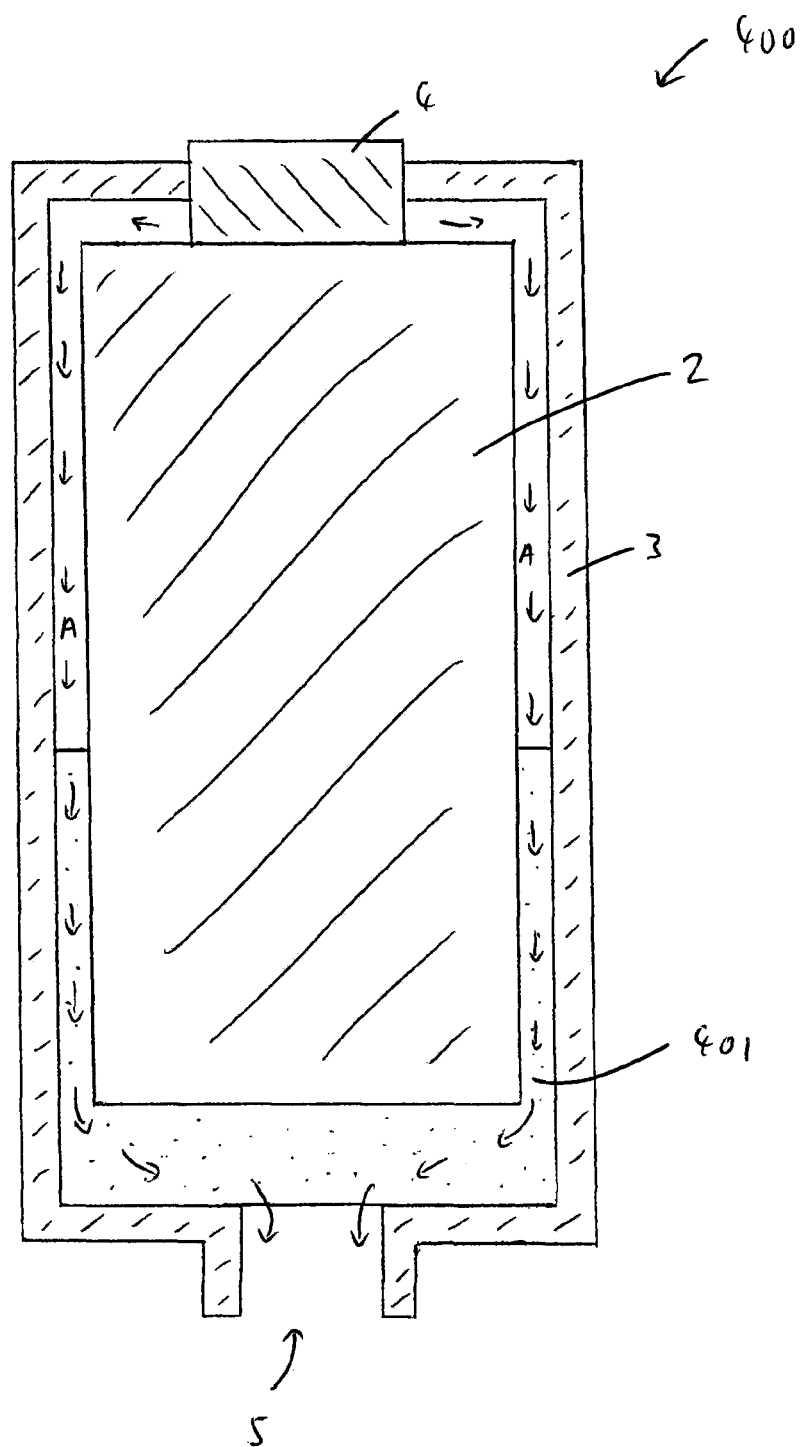
FIG. 6 is a cross-sectional view of an oxygen candle according to a third embodiment of the invention.

An oxygen candle in accordance with a third embodiment of the invention is now described with reference to FIG. 6. The oxygen candle 400 of the third embodiment is again similar to the oxygen candle 100 of the first embodiment, expect that instead of the chemical core 101 the oxygen candle 400 comprises the cylindrical chemical core 2 of the known oxygen candle 1. The oxygen candle 300 also comprises a cup-shaped filter 401, except that necessarily the gap that the filter 102 extends up into is only the smaller gap between the insulated housing 3 and the cylindrical chemical core 2.

While again this is a less advantageous configuration than that of the oxygen candle 100, the presence of the filter 401 around the sides of the chemical core 2 can still result in a steadier and a longer supply of oxygen, and a more effective removal of unwanted reaction products, compared to the known oxygen candle 1.

Whilst the present invention has been described and illustrated with reference to particular embodiments, it will be appreciated by those of ordinary skill in the art that the invention lends itself to many different variations not specifically illustrated herein.

What is claimed is:

1. A chemical core for an oxygen generator, the chemical core being capable on ignition of producing oxygen by chemical reaction, the chemical core comprising:
   a first cylindrical portion;
   a tapered portion; and a second cylindrical portion of smaller cross-sectional area than the first cylindrical portion, wherein:

the first cylindrical portion is positioned at a first end of the chemical core, the second cylindrical portion is positioned at a second end of the chemical core, and the tapered portion is positioned between the first cylindrical portion and the second cylindrical portion, and the first end of the chemical core has a larger cross-sectional area than the second end of the chemical core such that the ratio of the cross-sectional area of the first end to the cross-sectional area of the second end is 1.20:1 or more.

2. A chemical core as claimed in claim 1, comprising metal chlorate or perchlorate.

3. A chemical core as claimed in claim 1, comprising a catalyst and a fuel.

4. An oxygen generator comprising:

an insulated housing comprising a first end and a second end opposite the first end;

a chemical core as claimed in claim 1 positioned within the insulated housing so that the second end of the chemical core is at the second end of the insulated housing;

an ignition apparatus positioned at the first end of the insulated housing, for igniting a first end of the chemical core;

an oxygen outlet positioned at the second end of the insulated housing, for outputting oxygen produced by the chemical core;

a filter positioned within the second end of the insulated housing between the chemical core and the oxygen outlet, the filter being capable of removing at least one reaction product produced by the chemical reaction of the chemical core.

5. An oxygen generator as claimed in claim 4, wherein the filter is cylindrical.

6. An oxygen generator as claimed in claim 4, wherein the filter extends towards the first end of the insulated housing between the outer surface of the chemical core and the inner surface of the insulated housing.

7. An oxygen generator as claimed in claim 4, further comprising a cooling chamber positioned within the insulated housing having an inlet through which oxygen produced by the chemical core enters into the cooling chamber and an outlet through which cooled oxygen exits to the oxygen outlet.

* * * * *